United States Patent [19]

Lambert

[11] Patent Number: 4,666,437

[45] Date of Patent: * May 19, 1987

[54] HYDROPHILIC COATING

[75] Inventor: Hans R. Lambert, Askim, Sweden

[73] Assignee: Astra Meditec Aktiebolag, Sweden

[ * ] Notice: The portion of the term of this patent subsequent to Apr. 29, 2003 has been disclaimed.

[21] Appl. No.: 836,435

[22] Filed: Mar. 5, 1986

Related U.S. Application Data

[62] Division of Ser. No. 619,905, Jun. 12, 1984, Pat. No. 4,585,666.

[30] Foreign Application Priority Data

Apr. 22, 1982 [SE] Sweden ................................ 8202523

[51] Int. Cl.$^4$ .................. A61M 5/325; A61M 25/005; A01N 1/02
[52] U.S. Cl. ........................................ 604/265; 427/2; 427/412.1; 427/412.5; 428/423.7; 428/424.2; 428/424.4; 523/105; 523/113
[58] Field of Search ...................... 427/2, 412.1, 412.5; 604/280, 265; 523/105, 113; 428/423.7, 424.2, 424.4

[56] References Cited

U.S. PATENT DOCUMENTS

| | | | |
|---|---|---|---|
| 3,005,728 | 10/1961 | Bridgeford | 428/424.2 |
| 3,023,126 | 2/1962 | Underwood | 428/424.2 |
| 3,198,692 | 8/1965 | Bridgeford | 428/424.2 |
| 3,216,983 | 11/1965 | Shelanski et al. | 260/88.3 |
| 3,661,634 | 5/1972 | Riley et al. | 264/49 X |
| 4,100,309 | 7/1978 | Micklus et al. | 427/2 |
| 4,119,094 | 10/1978 | Michlus et al. | 428/35 X |
| 4,128,600 | 12/1978 | Skinner et al. | 427/44 X |
| 4,373,009 | 2/1983 | Winn | 428/424.2 |

FOREIGN PATENT DOCUMENTS 47-19193  2/1972  Japan .

OTHER PUBLICATIONS

"Transport Properties of Polyvinylpyrolidone-Polyisocyanate Interpolymer Membranes", *Desalination*, 8, (1970), pp. 177–193, R. L. Riley, C. R. Lyons and U. Merten.

"Hydrogels for Medical and Related Applications", *American Chemical Society, Symposium Series* 31, 1976, Buddy D. Ratner and Allan S. Hoffman, pp. 1–36.

*Primary Examiner*—Michael R. Lusignan
*Attorney, Agent, or Firm*—Brumbaugh, Graves, Donohue & Raymond

[57] ABSTRACT

A process for coating a polymer surface with a hydrophilic coating with low friction in wet condition. The process comprises applying to the polymer surface a solution containing between 0.05 to 40% of a compound which comprises at least two unreacted isocyanate groups per molecule, evaporating the solvent, applying a solution containing between 0.5 to 50% of polyvinylpyrrolidone to the thus treated polymer surface and then evaporating the solvent of the last mentioned solution, and curing the coating at elevated temperature. The process is preferably carried out in the presence of a catalyst for the curing of isocyanate.

9 Claims, No Drawings

HYDROPHILIC COATING

This application is a division of application Ser. No. 619,905, filed on June 12, 1984, now U.S. Pat. No. 4,589,666, patented Apr. 19, 1986.

The present invention relates to a process for coating a polymer surface with a hydrophilic coating which has a low coefficient of friction when wetted with a water based liquid, as well as medical articles being coated with a hydrophilic coating according to said process.

PRIOR ART

British Pat. No. 1 600 963 (Biosearch Medical Products Inc.) discloses a process for applying a hydrophilic coating which coating consists of an interpolymer of polyvinylpyrrolidone and polyurethane, said coating having a much lower coefficient of friction in wet condition than in dry condition. Such coatings are, among other things, especially useful for medical instruments intended to be entered in body cavities, because the instrument gives a good hand grip in dry condition while simultaneously becoming very slippery when it gets in contact with body liquids or wet mucuous membranes, and thus can be inserted easily without damage to the patient. The process disclosed in said British patent has been shown to be useful for accomplishing such coatings, but is on the other hand too complicated for being suitable for large-scale production. The process described in Example 1 in the patent thus comprises not less than ten steps, whereby one of the steps takes 6 hours to carry through. A further disadvantage with this known process is that cracks are often formed in the coating.

DISCLOSURE OF THE INVENTION

The object of the invention is to provide a process for the preparation of a hydrophilic coating that has a much lower coefficient of friction in wet condition and which process is more simple and more rapid to carry out than the process disclosed in the above-mentioned British Pat. No. 1 600 963. These objects of the invention have suprisingly been achieved by applying a solution containing between 0.05–40% (weight/volume, that is kg/liter) of a compound containing at least two unreacted isocyanate groups per molecule to a polymer surface, evaporating the solvent, applying a solution of polyvinylpyrrolidone containing between 0.5 to 50% (weight/volume) to the thus treated polymer surface and then evaporating the solvent of the last mentioned solution, and curing the coating at elevated temperature.

The invention is explained in detail in the following.

The process according to the invention can be used for coating many different types of polymer surfaces, such as latex rubber, other rubbers, polyvinylchloride, other vinyl polymers, polyesters and polyacrylates. The process has been found to be especially useful for latex, polyvinylchloride.

The process according to the invention comprises applying to a polymer surface a compound containing at least two unreacted isocyanate groups per molecule dissolved in a solvent, by dipping, spraying or the like and then evaporating the solvent preferably by air drying. This step forms a coating with unreacted isocyanate groups on the polymer surface. Examples of isocyanate containing compounds that may be used are polyisocyanates such as polymethylene polyphenyl isocyanate, 4,4'-diphenylmethane diisocyanate, and 2,4-toluene diisocyanate. Prepolymers or other addition products of isocyanates are especially useful, for example prepolymers of trimerized hexamethylene diisocyanate biuret. Such prepolymers are commercially available under the trade name Desmodur (Bayer AG).

The solvent for the isocyanate compound is preferably one that does not react with isocyanate. The preferred solvent is methylene chloride but it is also possible to use ethylacetate, acetone, chloroform, methyl ethyl ketone and ethylene dichloride, for example.

The isocyanate solution may advantageously contain between 0.5 to 10% (weight/volume) of isocyanate compound, and may preferably contain between 1 to 6% (weight/volume) of isocyanate compound. Generally, the solution need to be in contact with the surface only briefly, for example 5 to 60 seconds. In the case of coating of for example rubber latex it is desirable with a longer period, for example 1 to 100 minutes, to obtain a strong adherence. Another method to increase the adherence is to swell the polymer surface beforehand in a suitable solvent. A still further method is to choose a solvent for the isocyanate, such that the solvent in itself has the ability to swell or dissolve the polymer surface which is to be coated.

Following the evaporation of the solvent for the isocyanate from the polymer surface, the surface is coated with polyvinylpyrrolidone dissolved in a solvent, whereby a hydrophilic surface is obtained which subsequent to final curing of the isocyanate normally consists of a polyvinylpyrrolidone -polyurea interpolymer. The polyvinylpyrrolidone used should have a mean molecular weight of between $10^4$ to $10^7$, and the preferred mean molecular weight is about $10^5$. Polyvinylpyrrolidone having such a molecular weight is commercially available, for example under the trade name KOLLIDON ® (BASF). Examples of suitable solvents for polyvinylpyrrolidone that can be used are methylene chloride (preferred), ethyl acetate, acetone, chloroform, methyl ethyl ketone and ethylene dichloride. The proportion of polyvinylpyrrolidone in the solution is preferably between 0.5 to 10% (weight/volume) and most preferred between 2 to 8% (weight/volume). The polyvinylpyrrolidone in the solvent is applied by dipping, spraying or the like for a short period of time, for example during 5 to 50 seconds. After the polyvinylpyrrolidone solution has been applied to the coated surface, the solvent is evaporated preferably by air drying. The residual traces of solvent are removed at the curing of the coating which is preferably performed at a temperature of 50° to 100° C., in for example an oven, and during 5 to 30 minutes. All the other steps in the process may be performed at ambient temperature.

The purpose of the curing, which is advantageously conducted in the presence of a water-containing gas such as ambient air, is to bind the isocyanate compounds together to the formation of a stable non-reactive network that binds the hydrophilic polyvinylpyrrolidone. The isocyanate groups reacts with water at the curing and yields an amine which rapidly reacts with other isocyanate groups to the formation of a urea cross-link.

According to the invention it has suprisingly been found possible to simultaneously reduce the low friction of the hydrophilic surface, to improve the adherence of the coating, and to shorten the necessary reaction times and curing times, by using some additives to the solution of isocyanate and/or the solution of polyvinylpyrrolidone. Such a suitable additive comprises different known catalysts for isocyanate curing. These catalysts may be dissolved in either the isocyanate solution or the polyvinylpyrrolidone solution but are preferably dissolved in the latter. Different types of amines are especially useful, for example different diamines, but also for example triethylene diamine. Preferably, an aliphatic amine is employed which is volatilizable at the drying and curing temperatures used for the coating, and which furthermore is non-toxic. Examples of suitable amines are N, N'-diethylethylendiamine, hexamethylendiamine, ethylendiamine, paradiaminobenzene, 1,3-propandiol-para-aminobenzoic acid diesther, diaminobicyclo octane, and triethanolamine. The proportion of catalyst in the polyvinylpyrrolidone solution is suitably between 0.1 to 50% by weight of the amount of polyvinylpyrrolidone, preferably between 0.1 to 10% by weight. Some of the above-mentioned amines, particularly the diamines, can also react with isocyanate and thereby contribute to the cross-linking of the isocyanate compounds that give the desired strong adherence between the hydrophilic coating and the polymer surface.

Furthermore, it has surprisingly been shown to be possible to reduce the low friction for the hydrophilic surface still further, by way of dissolving a polymer in the isocyanate solution. Examples of suitable polymers are polyesters, polyvinyl compounds such as polyvinylchloride or polyvinylacetate, [polyurethanes, polyisocyanates,] or copolymers of these. These otherwise substantially inert polymers are supposed to give the surprisingly reduced friction at the surface mainly because they obstruct an undesired diffusion of not yet cross-linked isocyanate compounds out into the polyvinylpyrrolidone layer. A further reason for the low friction may be that the addition of a polymer enhance the elasticity of the coating. The proporation of dissolved polymer in the isocyanate solution is suitably between 0.5 to 20% by weight of the solution, preferably between 2 to 10% by weight.

The obtained hydrophilic coating evidently contains an appreciable amount of partly freely movable polyvinylpyrrolidone chains. Thus it has been shown that the coating can complex-bind a substantial amount of elemental iodine (compare Example 6), as is also the case with free polyvinylpyrrolidone. Such a iodine containing hydrophilic and antibacterial coating is advantageous for many medical uses, for example for urinary catheters which are intended for insertion in the urethra for extended periods of time and which otherwise is a common cause of infections. The iodine containing coating is suitably prepared by final dipping in a $KI/I_2$-solution containing at least 1% by weight of iodine, followed by drying, possibly preceeded by rinsing in a solvent.

The invention is illustrated in detail in the following Examples.

EXAMPLE 1

A pentamer of hexamethylene diisocyanate and toluene diisocyanate of cyanurate type (named Desmodur HL; Bayer AG) was dissolved in methylene chloride to a concentration of 3% (weight/volume). A urinary PVC catheter was dipped in this solution during 5 seconds. The catheter was allowed to dry at ambient temperature during 30 seconds, whereupon it was dipped during 5 seconds in a solution containing 6% (weight/volume) of polyvinylpyrrolidone (K90; mean molecular weight~360 000) and 0.6% (weight/volume) of triethylene diamine (DABCO ®), dissolved in methylene chloride. The catheter was then allowed to dry at ambient temperature during 60 seconds, and then cured during 20 minutes at 70° C. above a bowl filled with water. The catheter was finally allowed to cool to ambient temperature during 20 minutes whereupon it was rinsed in water. The catheter had a slippery and adherent surface when wet.

This experiment was repeated without any triethylene diamine being added, and in that case no slippery surface was obtained.

EXAMPLE 2

A trimerized hexamethylene diisocyanate of biuret type (named Desmodur L 2291; Bayer AG) was dissolved in methylene chloride to a concentration of 6% (weight/volume). A urinary PVC catheter was dipped in this solution during 30 seconds. The catheter was then dried at 70° C. during 60 seconds, whereupon it was dipped during 5 seconds in a solution containing 33 g polyvinylpyrrolidone (K25; mean molecular weight~25 000) per 100 ml methylene chloride. This solution also contained 0.33 g triethylene diamine (DABCO ®) per 100 ml solution. The catheter was then allowed to dry at ambient temperature during 60 seconds, and then cured during 40 minutes at 70° C. above a bowl filled with water. The catheter was finally allowed to cool to ambient temperature and was then rinsed in water. The catheter had a slippery and adherent surface when wet.

This experiment was repeated without any triethylene diamine being added, and in that case no slippery surface was obtained, even if the curing time was increased to 6 hrs at 70° C.

EXAMPLE 3

A trimerized hexamethylene diisocyanate of biuret type (named Desmodur L 2291; Bayer AG) was dissolved in methylene chloride to a concentration of 6% (weight/volume). A catheter made of softened PVC was dipped in this solution during 5 seconds. The catheter was then dried at ambient temperature during 30 seconds, whereupon it was dipped during 5 seconds in a solution containing 6% (weight/volume) of polyvinylpyrrolidone (K90; mean molecular weight~360 000) and 1% (weight/volume) of N,N'-diethyl-ethylene diamine, dissolved in methylene chloride. The catheter was then allowed to dry at ambient temperature during 30 seconds and was then cured in an oven during 3 hrs at 70° C. The catheter was finally rinsed in water during one hour at ambient temperature. The catheter had a slippery and adherent surface when wet.

The experiment was repeated without any amine being added and in that case the hydrophilic surface was not adherent and disappeared when the catheter was rinsed in water.

EXAMPLE 4

A trimerized hexamethylene diisocyanate of biuret type (named Desmodur L 2291; Bayer AG) was dissolved in methylene chloride to a concentration of 6% (weight/voluem). A urinary PVC catheter was dipped in this solution during 30 seconds and was then dried at ambient temperature during 30 seconds. The catheter was then dipped during 5 seconds in a solution containing 6% (weight/volume) of polyvinylpyrrolidone (K90; mean molecular weight~360 000) and 2.5% (weight/volume) of triethylamine, dissolved in methylene chloride. The catheter was then allowed to dry at ambient temperature during 30 seconds and was finally cured in an oven during 5 minutes at 70° C. The catheter had a slippery and adherent surface when wet.

The experiment was repeated with variations in curing time of from 5 to 20 minutes, and it was found that a surface with optimum properties as to low friction and adherence was obtained after only 5 minutes curing time.

EXAMPLE 5

A trimerized hexamethylene diisocyanate of biuret type (namde Desmodur L 2291; Bayer AG) was dissolved in methylene chloride to a concentration of 6% (weight/volume). A urinary latex catheter was dipped in this solution during 30 seconds and was then dried at ambient temperature during 30 seconds. The catheter was then dipped during 5 seconds in a solution containing 6% (weight/volume) of polyvinylpyrrolidone (K90; mean molecular weight ~360 000) and 0.6% (weight/volume) of triethylamine, dissolved in methylene chloride. The catheter was then allowed to dry at ambient temperature during 30 seconds and was finally cured during 20 minutes at 70° C. above a bowl filled with water. The catheter was finally allowed to cool to ambient temperature and was then rinsed in water and 0.2 M HCl (aq.). The catheter had a slippery and adherent surface when wet.

The experiment was repeated with variations in dipping time in the isocyanate bath of from 30 seconds to 10 minutes, but no advantages was obtained by increasing the dipping time beyond 30 seconds.

EXAMPLE 6

The inner of a two meter long hose of PVC (inner diameter 8 mm; out diameter 10 mm) was flushed with different solutions and drying agents in the following orders and periods of time:

6% (weight/volume) of a trimerized hexamethylene diisocyanate of biuret type (named Desmodur L 2291; Bayer AG) dissolved in methylene chloride and during 30 seconds; a stream of ambient air during 30 seconds; 6% (weight/volume) of polyvinylpyrrolidone (K90; mean molecular weight ~360 000) and 0.06% (weight/volume) of triethylamine, dissolved in methylene chloride and during 10 seconds; a stream of ambient air during 30 seconds.

The hose was then cured in an oven during 6 hrs at 70° C., and was then flushed with a saturated water solution of potassium iodide being saturated with elemental iodine. A section of the hose was cut open and the inside of the hose was found to be coated with a brown iodine-containing surface which was slippery when wet and which adhered to the surface even after extended soaking in water.

The experiment was repeated without an triethylamine being added and it was found that no adherent coating was being formed.

EXAMPLE 7

In this experiment pieces (50×120 mm in size) of the following different plastic film materials were treated according to the invention and tested:
(a) low density polyethylene, LOPE,
(b) plasma treated low density polethylene, PT-LDE,
(c) ethylene - 2.5% vinyl acetate copolymer,
(d) ethylene - 5% vinyl acetate copolymer,
(e) ethylene - 18% vinyl acetate copolymer,
(f) ethylene - 3% butyl acrylate copolymer,
(g) ethylene - 7% butyl acrylate copolymer,
(h) ethylene - 17% butyl acrylate copolymer,
(i) SURLYN (Trade Mark) (from Dupont).

The film pieces were treated with a solution of 2% diphenylmethane-4,4'-diisocyanate in a mixture of 25% trichloroethylene and 75% methylene chloride for 15 seconds. Then the pieces were dried for 30 seconds and treated with a solution of 6% polyvinylpyrrolidone in a mixture of 25% trichloroethylene and 75% methylene chloride for 3 seconds. The film pieces were heated in an oven for 6 hours at 70° C.

After this the film pieces were wetted in water and the surface was tested for lubricity. The films of SURLYN (Trade Mark), butyl acrylate copolymers and vinyl acetate copolymers were found to have a permanent surface with very low friction when wet. The other films had low friction surface although the surface was not as durable.

I claim:

1. A process for placing on a polymer surface a hydrophilic coating which has a low coefficient of friction when wetted with a water-based liquid, which consists essentially of applying a solution to the surface of an article made from a polymer selected from the group consisting of rubber, vinyl polymers, polyesters and polyacrylates, which solution consists essentially of an organic solvent and a solute in an amount of between 0.05 to 40% (weight to volume), said solute consisting essentially of an isocyanate monomer having at least 2 unreacted isocyanate groups per molecule, an isocyanate prepolymer thereof having up to 5 monomer units, or a mixture of such monomers and prepolymers, evaporating the solvent, applying a second solution consisting essentially of a solvent containing between 0.5 to 10% (weight to volume) of polyvinyl pyrrolidone to the thus treated polymer surface, and then evaporating the solvent of the second solution and curing the coating in the presence of a water-containing gas at elevated temperature.

2. A process according to claim 1 wherein the isocyanate is selected from the group consisting of toluene diisocyanate, hexamethylene diisocyanate and 4,4'-diphenyl-methane diisocyanate.

3. A process according to claim 1 wherein the polymer surface to be coated comprises a polymer selected from the group consisting of latex rubber and polyvinylchloride.

4. A process according to claim 2 wherein the hydrophilic coating is treated with iodine.

5. A medical article for insertion in the body which is provided with a hydrophilic coating prepared in accordance with a process which consists essentially of applying a solution to the surface of an article made from a polymer selected from the group consisting of rubber, vinyl polymers, polyesters and polyacrylates, which solution consists essentially of an organic solvent and a solute in an amount of between 0.05 to 40% (weight to volume), said solute consisting essentially of an isocyanate monomer having at least 2 unreacted isocyanate groups per molecule, an isocyanate prepolymer thereof having up to 5 monomer units, or a mixture of such monomers and prepolymers, evaporating the solvent, applying a second solution consisting essentially of a solvent containing between 0.5 to 10% (weight to volume) of polyvinyl pyrrolidone to the thus treated polymer surface, and then evaporating the solvent of the second solution and curing the coating in the presence of a water-containing gas at elevated temperature.

6. A medical article according to claim 5 wherein the isocyanate is selected from the group consisting of toluene diisocyanate, hexamethylene diisocyanate and 4,4'-diphenylmethane diisocyanate.

7. A medical article according to claim 5 wherein the polymer surface to be coated comprises a polymer selected from the group consisting of latex rubber and polyvinylchloride.

8. A medical article according to claim 6 wherein the hydrophilic coating is treated with iodine.

9. A medical article according to claims 5, 6, 7 or 8 which comprises a catheter.

* * * * *